United States Patent [19]

Komaki et al.

[11] Patent Number: 4,581,535

[45] Date of Patent: Apr. 8, 1986

[54] METHOD OF RECORDING X-RAY IMAGE

[75] Inventors: Takao Komaki; Hirosi Tanaka; Nobuyoshi Nakajima, all of Minamiashigara, Japan

[73] Assignee: Fuji Photo Film Co., Ltd., Kanagawa, Japan

[21] Appl. No.: 433,719

[22] Filed: Oct. 12, 1982

[30] Foreign Application Priority Data

Oct. 16, 1981 [JP] Japan .............................. 56-165116
Oct. 16, 1981 [JP] Japan .............................. 56-165121
Jun. 25, 1982 [JP] Japan .............................. 57-109637

[51] Int. Cl.$^4$ ............................................. G03C 5/16
[52] U.S. Cl. .............................. 250/327.2; 250/484.1; 250/486.1; 378/23
[58] Field of Search ................. 250/327.2, 484.1, 337, 250/486.1; 378/174, 19, 23, 2; 364/414

[56] References Cited

U.S. PATENT DOCUMENTS

| | | | |
|---|---|---|---|
| 2,680,199 | 6/1954 | Abel | 378/174 |
| 3,291,983 | 12/1966 | Landau | 378/23 |
| 3,976,886 | 8/1976 | Landau | 378/174 |
| 4,284,889 | 8/1981 | Kato et al. | 250/337 |
| 4,356,398 | 10/1982 | Komaki et al. | 250/327.2 |

Primary Examiner—Carolyn E. Fields
Attorney, Agent, or Firm—Gerald J. Ferguson

[57] ABSTRACT

A stack of many stimulable phosphor sheets and an X-ray tube are positioned with an object intervening therebetween, and moved with respect to each other around a tomographic plane in the object so as to satisfy the linear rule and the geometric rule in the course of exposure of the object to X-rays, thereby storing images of many tomographic planes in the stimulable phosphor sheets in a single recording step. The respective stimulable phosphor sheets are then exposed to a stimulating ray to cause them to emit light, the emitted light is photoelectrically read out, and the obtained electric signals are reproduced as visible tomographic images usable in diagnosis with high efficiency and accuracy. The electric signals may be superposed one upon another and reproduced as an X-ray image of any slice thickness, particularly a slice thickness of 5 mm or more, which is free from interfering shadows.

22 Claims, 4 Drawing Figures

METHOD OF RECORDING X-RAY IMAGE

BACKGROUND OF THE INVENTION

1. Field of the Invention

This invention relates to a method of recording an X-ray image, and more particularly to a method of recording an X-ray image by use of a stimulable phosphor sheet.

2. Description of the Prior Art

For medical diagnosis, there is generally used radiography in which a radiation image of an object is obtained by exposing the object to X-rays and recording the X-rays transmitting through the object on an X-ray photographic film. In conventional radiography, since a radiation image of the whole object is recorded, the obtained radiograph is sometimes adversely affected by an interfering shadow overlapping upon the image of a portion of the object under examination. For example, when the lungs are radiographed, a shadow of the rib overlaps upon the image of the lungs recorded, making it difficult to correctly diagnose the area of disease in the lungs. When abdomenal organs are radiographed, gas contained in the intestines forms a shadow overlapping on the image of the abdomenal organs and adversely affecting the diagnosis of the organs.

To eliminate the interfering shadows encountered in conventional radiography, it has been proposed to conduct tomography in which an image of only a desired tomographic plane in an object is sharply formed on an X-ray photographic film while images of the other planes in the object are made unsharp. In tomography, an X-ray tube and an X-ray photographic film are opposed to each other with an object therebetween, and moved with respect to each other around the object at the time of exposing the object to X-rays so as to satisfy the linear rule and the geometric rule. The linear rule specifies that the focal point of the X-ray tube, one point on the tomographic plane in the object, and one point on the X-ray film must be on the same straight line. The geometric rule specifies that the ratio of the distance between the focal point of the X-ray tube and the tomographic plane in the object to the distance between the tomographic plane and the X-ray film must be maintained constant.

Recently, it has been proposed to conduct simultaneous multilayer tomography in which recording is effected in the same way as described above by stacking a plurality of combinations of an X-ray photographic film and two X-ray intensifying screens to simultaneously obtain images of a plurality of tomographic planes in an object on the respective X-ray photographic films of said combinations.

In tomography, the X-ray tube and the combinations may be moved along linear, circular, elliptical or spiral paths insofar as the linear rule and the geometric rule described above are satisfied. Tomographic techniques are described in detail, for example, in "Hoshasen Gijutsu No Tebiki" (Guide to Radiation Technology) published by the Tokyo Radiation Engineers' Association.

FIG. 1 schematically shows conventional simultaneous multilayer tomography in which an X-ray tube and combinations of an X-ray photographic film and X-ray intensifying screens are moved along horizontal linear paths. An X-ray tube 1 and a cassette 3 containing a stack of X-ray photographic films 2a, 2b and 2c are opposed to each other on both sides of an object 4. The X-ray photographic films 2a, 2b and 2c are provided with X-ray intensifying screens (not shown) so that a lower film exhibits a higher sensitivity to X-rays than an upper film.

In the recording step, the object 4 is exposed to X-rays emitted from the X-ray tube 1 while the X-ray tube 1 and the cassette 3 are moved in the directions of the arrows 5 and 6, respectively. In this way, an image of a tomographic plane 8a which is defined by the intersections of X-rays 7a and 7a', respectively, formed as the X-ray tube 1 is moved in the direction of the arrow 5 is formed on the X-ray photographic film 2a. Similarly, an image of a tomographic plane 8c which is defined by the intersections of X-rays 7c and 7c', respectively, formed as the X-ray tube 1 is moved is formed on the X-ray photographic film 2c.

In simultaneous multilayer tomography, images of a plurality of tomographic planes in an object can be recorded on X-ray photographic films by a single recording step. Accordingly, for moving organs such as the heart and lungs, it is possible to obtain tomographic images in exactly the same motion phase. For stationary organs, it is possible to obtain images of a plurality of tomographic planes, which are free from adverse effects due to movement of the object in the course of tomography. Furthermore, simultaneous multilayer tomography reduces the X-ray dose to the object (patient) and reduces the physical and mental burden on the patient.

However, in conventional simultaneous multilayer tomography, X-rays transmitting through the object are attenuated as they sequentially transmit through a plurality of combinations of an X-ray photographic film and X-ray intensifying screens, so that an upper X-ray photographic film exhibits a higher image density and a lower one a lower image density. Therefore, it is necessary to compensate for the fluctuation in image density among the X-ray photographic films by adjusting the sensitivities of the combinations of the X-ray photographic film and the intensifying screens. In general, however, it is very difficult to adjust the sensitivities thereof according to respective objects. Further, the sensitivity of the lowermost combination can be increased only to a limited extent, i.e. only to an insufficient level. In addition, X-rays of lower energy are absorbed in an upper combination and do not reach a lower one, and X-rays of higher energy travel a longer distance to a lower combination. Accordingly, an upper X-ray photographic film exhibits a higher contrast and a lower one a lower contrast, necessitating adjustment of the gamma values of the X-ray photographic films. However, it is very difficult to prepare X-ray photographic films with gamma values adjusted according to the respective objects. For the reasons mentioned above, it is generally extremely difficult to obtain X-ray images which can be used for diagnosis with high efficiency and accuracy with conventional simultaneous multilayer tomography. Further, in conventional simultaneous multilayer tomography, at most only four or five layers of the combinations of the X-ray photographic film and intensifying screens can be stacked and used for tomography. Therefore, to obtain more tomographic images, it is necessary to conduct the recording step many times.

As a method of obtaining an X-ray image of an arbitrary slice thickness of an object, it has been proposed to change the distances of the movements of the X-ray tube and the combinations conducted with respect to each other around a tomographic plane of the object so as to satisfy the linear rule and the geometric rule described above. In this method, images of a small slice thickness of the object are obtained when the distances of the movements of the X-ray tube and the combinations with respect to each other are increased, and images of a large slice thickness of the object are obtained when the distances of the movements thereof are small. However, when the X-ray tube and the combinations are moved a short distance with respect to each other to obtain X-ray images of a large slice thickness, e.g. 5 mm or more, shadows detrimental to diagnosis are not eliminated completely from the X-ray images, and the effects of tomography cannot be achieved. Thus, with this method, it is extremely difficult to obtain X-ray images of an arbitrary slice thickness, particularly 5 mm or more, which are free from the shadows interfering with diagnosis.

SUMMARY OF THE INVENTION

The primary object of the present invention is to provide a method of recording an X-ray image, in which tomographic images usable in diagnosis with high efficiency and accuracy can be obtained easily.

Another object of the present invention is to provide a method of recording an X-ray image, in which very many tomographic images can be obtained in a single recording step.

A further object of the present invention is to provide a method of recording an X-ray image, in which X-ray images of an arbitrary slice thickness of an object can be recorded without any interfering shadows.

The specific object of the present invention is to provide a method of recording an X-ray image, in which X-ray images of a slice thickness of 5 mm or more can be recorded without any interfering shadows.

The method in accordance with the present invention comprises the steps of positioning a stack of a plurality of stimulable phosphor sheets and an X-ray tube with an object intervening therebetween, and moving said stack and said X-ray tube with respect to each other around a tomographic plane in said object so as to satisfy the linear rule and the geometric rule in the course of exposure of said object to X-rays, exposing the respective stimulable phosphor sheets to a stimulating ray to cause them to emit light, photoelectrically reading out the light emitted from said stimulable phosphor sheets upon stimulation thereof, and recording an X-ray image using the obtained electric signal.

The present invention also provides a method comprising the steps of positioning a stack of a plurality of stimulable phosphor sheets and an X-ray tube with an object intervening therebetween, moving said stack and said X-ray tube with respect to each other around a tomographic plane in said object so as to satisfy the linear rule and the geometric rule in the course of exposure of said object to X-rays, exposing the respective stimulable phosphor sheets to a stimulating ray to cause them to emit light, photoelectrically reading out the light emitted from said stimulable phosphor sheets upon stimulation thereof, and superposition-processing the obtained electric signals, and recording an X-ray image using the obtained superposition-processed electric signal.

In the present invention, the stimulable phosphor sheet is provided with a layer of a stimulable phosphor. The stimulable phosphor has such properties that, when exposed to such radiation as X-rays, $\alpha$-rays, $\beta$-rays, $\gamma$-rays or ultraviolet rays, the stimulable phosphor stores a part of the energy of the radiation. Then, when the phosphor which has been exposed to the radiation is exposed to a stimulating ray such as visible ray, light is emitted from the phosphor in the pattern of the stored energy of the radiation.

The Applicant proposed in his U.S. Pat. No. 4,258,264 and Japanese Unexamined Patent Publication No. 56(1981)-11395 a radiation image system in which the stimulable phosphor sheet is first exposed to a radiation transmitting through an object to have a radiation image stored therein, and is then scanned with a stimulating ray such as laser beam which causes it to emit light in the pattern of the stored image. The light emitted from the stimulable phosphor sheet upon stimulation thereof is photoelectrically detected and converted to an electric image signal, which is processed as desired to reproduce a visible image on a recording medium such as photographic light-sensitive material or on a display such as cathode ray tube (CRT).

This radiation image system using the stimulable phosphor sheet is advantageous over conventional radiography using a combination of a silver halide X-ray photographic material and intensifying screens in that the image can be recorded over a very wide range of radiation exposure and further in that the electric signal used for reproducing the visible image can be freely processed to improve the image quality for viewing and diagnostic purposes. In more detail, since the amount of light emitted upon stimulation after the radiation energy is stored in the phosphor varies over a very wide range in proportion to the amount of energy stored therein, it is possible to obtain an image having desirable density regardless of the amount of exposure of the phosphor to the radiation by reading out the emitted light with an appropriate read-out gain and converting it to an electric signal to reproduce a visible image on a recording medium or a display. The electric signal may further be processed as desired to obtain a radiation image suitable for viewing and diagnostic purposes. This is very advantageous in practical use.

As mentioned above, in the radiation image system using a stimulable phosphor, deviation of the level of the radiation energy stored in the stimulable phosphor from a desired level can easily be compensated for by photoelectrically reading out the light emitted from the stimulable phosphor upon stimulation thereof by setting the read-out gain to an appropriate value. Therefore, in the method using the stimulable phosphor in accordance with the present invention, it is not necessary to adjust the sensitivities of the respective layers of the X-ray photographic films and the intensifying screens, which is necessitated in the conventional simultaneous multilayer tomography. Namely, in the present invention, the respective stimulable phosphor sheets of the stack may have the same sensitivity, and it is not always necessary to strictly adjust the sensitivities of the stimulable phosphor sheets with reference to one another even when changing them. Further, in the present invention, since the total thickness of the stack of the stimulable phosphor sheet is smaller than that of the conventional stack of the combinations of the X-ray film and the intensifying screens, and compensation for the sensitivities of the stimulable phosphor sheets can be effected by appropriately setting the read-out gain, it is possible to increase the number of stimulable phosphor sheets of the stack, i.e. to obtain more tomographic images with one recording step than in the conventional method. Furthermore, since it is possible to easily compensate the contrast of the obtained radiation image by processing the gradation of the photoelectrically read-out image signal, the present invention can produce many tomographic images of the same contrast without any necessity for strictly adjusting the gamma values of the X-ray photographic films as is required in the case of the conventional simultaneous multilayer tomography.

According to another embodiment of the present invention, by using a plurality of stimulable phosphor sheets stacked in such a way that a phosphor sheet exhibiting a higher X-ray use efficiency is positioned farther from the object, the tomographic images having a higher diagnostic efficiency and accuracy and a uniform quality and greatly increase the number of tomographic images obtainable in a single recording step, can be obtained. The X-ray use efficiency means the efficiency for converting the given X-ray energy to light emitted upon stimulation of the stimulable phosphor. The X-ray use efficiencies of the respective phosphor sheets in a stack may be changed by changing the thickness of the phosphor layer of each phosphor sheet (since, in general, the X-ray use efficiency increases in proportion to the thickness of the phosphor layer), and/or changing the kind of the stimulable phosphor provided on each phosphor sheet.

In addition, since it is easy to conduct super-position processing of the image signals of the respective tomographic images, the present invention can produce an X-ray image of a slice thickness of, for example, 50 mm free from any interfering shadows by recording images of tomographic planes at 5 mm intervals and superposing the obtained image signals. In this way, it is possible to obtain an image of the lungs free from shadows of the rib or an image of the abdomenal organs free from shadows of gas contained in the intestines. This is extremely effective for diagnostic purposes. In the present invention, the superposition processing may be of the type disclosed, for example, in U.S. Pat. Application Ser. No. 168,800 now U.S. Pat. No. 4,356,348, and Japanese Unexamined Patent Publication No. 56(1981)-11400.

In the present invention, in order to improve the signal-to-noise ratio, it is preferable that the stimulable phosphor emit light having a wavelength range not overlapping upon the range of wavelength of the stimulating ray employed to excite the stimulable phosphor. Preferably, the stimulable phosphor should emit light having a wavelength within the range between 300 nm and 500 nm, and the wavelength of the stimulating ray should be within the range between 450 nm and 700 nm.

As the stimulable phosphor capable of emitting light having a wavelength within the range between 300 nm and 500 nm, for example, rare earth activated alkaline earth metal fluorohalide phosphor is preferred. One example of this phosphor is, as shown in Japanese Unexamined Patent Publication No. 55(1980)-12143, a phosphor represented by the formula $(Ba_{1-x-y},Mg_x,Ca_y)FX:aEu^{2+}$ wherein X is at least one of Cl and Br, x and y are numbers satisfying $0 < x+y \leq 0.6$ and $xy \neq 0$, and a is a number satisfying $10^{-6} \leq a \leq 5 \times 10^{-2}$. Another example of this phosphor is, as shown in U.S. Pat. No. 4,239,968, a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in this invention can be used ZnS:Cu,Pb; $BaO.xAl_2O_3$:Eu wherein $0.8 \leq x \leq 10$; and $M^{II}O.xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, and LnOX:xA wherein Ln is at least one of La, Y, Gd and Lu, X is at least one of Cl and Br, A is at least one of Ce and Tb, x is a number satisfying $0 < x < 0.1$, as shown in U.S. Pat. No. 4,236,078.

Among the above enumerated phosphor, the rare earth activated alkaline earth metal fluorohalide phosphor is the most preferable, among which barium fluorohalides are the most preferable in view of the high intensity of emission of light.

Further, barium fluorohalide phosphors added with a metal fluoride as disclosed in Japanese Unexamined Patent Publication Nos. 56(1981)-2385 and 56(1981)-2386, or barium fluorohalide phosphors containing at least one of a metal chloride, a metal bromide and a metal iodide as disclosed in Japanese Patent Application No. 54(1979)-150873 are also preferable because of their improved light emitting characteristics.

Since the X-ray use efficiency of a stimulable phosphor changes depending on the composition thereof, when a plurality of stimulable phosphor sheets stacked in such a way that a phosphor sheet exhibiting a higher X-ray use efficiency is positioned farther from the object, it is possible to constitute the phosphor sheets stack employed in the present invention by using two or more stimulable phosphors. For example, the phosphor sheets formed of the following stimulable phosphors may be stacked in the following order, starting from the top: (1) ZnS:Cu, Pb, (2) $M^{II}O.xSiO_2$:A, (3) $(Ba_{1-x-y},Mg_x,Ca_y)FX:aEu^{2+}$, $(Ba_{1-x},M^{II}_x)FX:yA$ and $BaO.xAl_2O_3$:Eu (the order of these phosphors changes according to a change in composition), and (4) LnOX:xA.

It is also desirable to color the phosphor layer of the stimulable phosphor sheet made of the above phosphor by use of pigments or dyes to improve the sharpness of the image obtained thereby as disclosed in U.S. patent application Ser. No. 156,520, now U.S. Pat. No. 4,394,581.

In the present invention, the gradation processing may be of the type disclosed in U.S. Pat. Nos. 4,302,672, 4,276,473 and 4,310,886. In order to improve the quality of the radiation image and the diagnostic efficiency and accurary, it is also possible to employ the frequency processing as disclosed in U.S. Pat. No. 4,346,295, U.S. Pat. No. 4,315,318, corresponding to Japanese Unexamined Patent Publication Nos. 56(1981)-75137 and 56(1981)-75139, in combination with the gradation processing mentioned above.

In the present invention, when the read-out gain should be adjusted and the photoelectrically converted image signal should be gradation-processed according to the radiation energy stored in the stimulable phosphor sheets of the stack, it is necessary to investigate in advance the radiation energy stored in the stimulable phosphor sheets. For this purpose, it is preferable to read the information of the radiation energy stored therein with a stimulating ray of low energy by using the method and system as disclosed in Japanese Patent Application Nos. 56(1981)-165111, 56(1981)-165112, 56(1981)-165113, 56(1981)-165114 and 56(1981)-165115, set the read-out gain and the gradation processing conditions on the basis of information thus read out, and finally scan the stimulable phosphor sheets with another stimulating ray to reproduce a visible radiation image based on the light emitted from the stimulable phosphor sheets. However, the information of the radiation energy stored in the stimulable phosphor sheets may be read out in advance by any other methods, for example by the instantaneous light emission method as disclosed in U.S. Pat. No. 4,284,889.

DESCRIPTION OF THE PREFERRED EMBODIMENTS

The present invention will hereinbelow be described in further detail with reference to the accompanying drawings.

Figure 2:
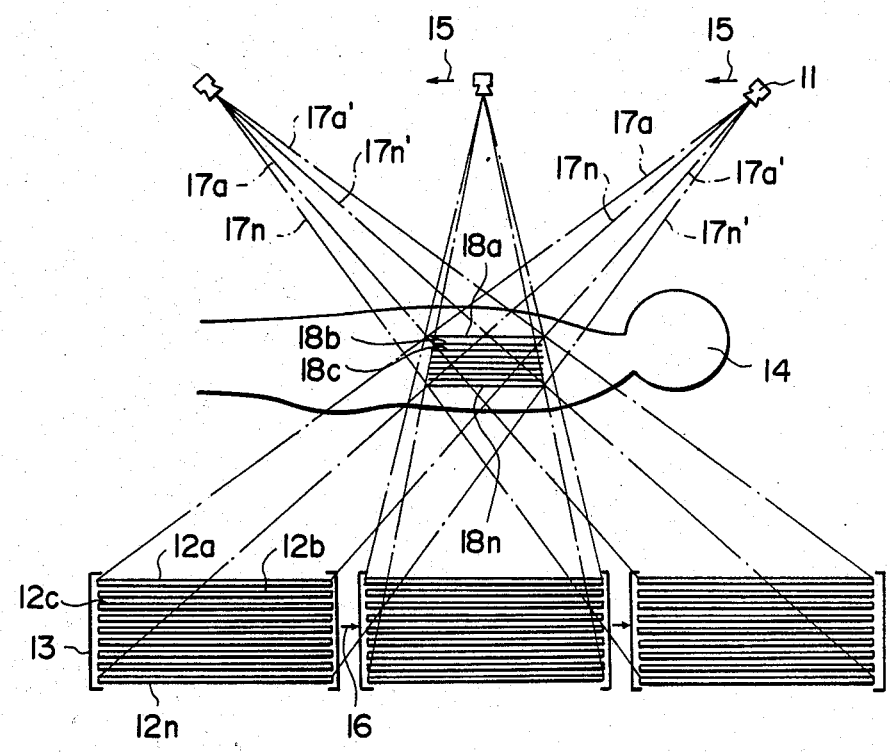
FIG. 2 is a schematic view showing an embodiment of the X-ray image recording method in accordance with the present invention.

Referring to FIG. 2 showing an embodiment of the method in accordance with the present invention, an X-ray tube 11 and a cassette 13 containing a stack of stimulable phosphor sheets 12a, 12b, 12c, ..., 12n are positioned on opposite sides of an object 14.

Figure 1:
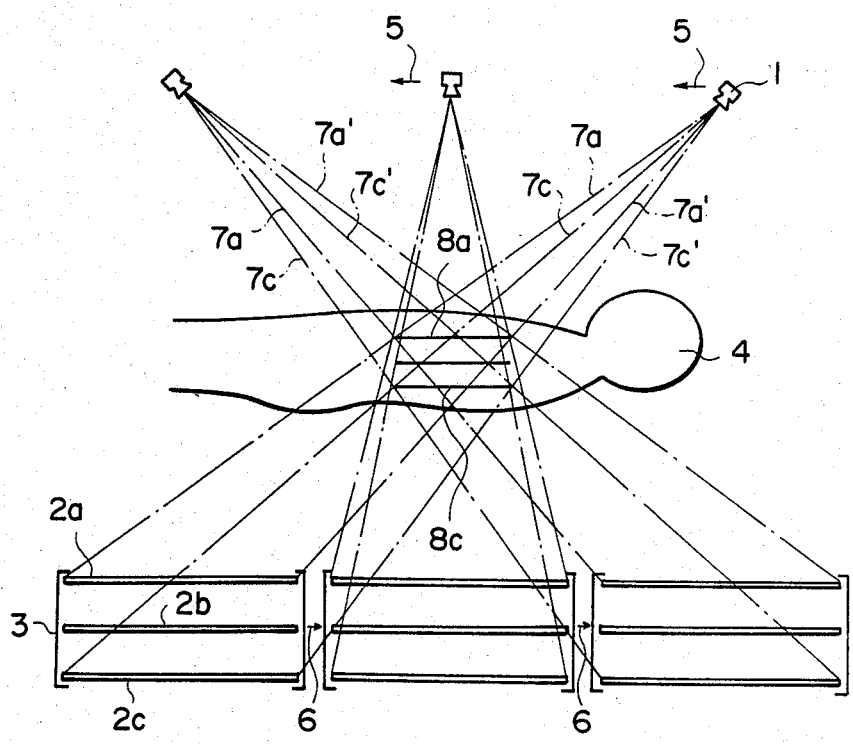
FIG. 1 is a schematic view showing conventional simultaneous multilayer tomography.

In the recording step, the object 14 is exposed to X-rays emitted from the X-ray tube 11 while the X-ray tube 11 and the cassette 13 are moved in the directions of the arrows 15 and 16, respectively. As a result, a tomographic image of a tomographic plane 18a of the object 14 is stored as the X-ray energy in the stimulable phosphor sheet 12a, and a tomographic image of a tomographic plane 18n of the object 14 is stored in the stimulable phosphor sheet 12n, similarly to what was described with reference to FIG. 1. At this stage, the tomographic images of the tomographic planes 18a, 18b, 18c, ..., 18n of the object 14 are stored in the stimulable phosphor sheets 12a, 12b, 12c, ..., 12n in such a manner that the tomographic image stored in an upper stimulable phosphor sheet would be reproduced as a visible image of a higher density and contrast than that in a lower stimulable phosphor sheet. The stimulable phosphor sheets 12a, 12b, 12c, ..., 12n carrying the tomographic images are then sent to a read-out system.

A further embodiment of the method in accordance with the present invention, using a plurality of stimulable phosphor sheets stacked in such a way that a phosphor sheet exhibiting a higher X-ray use efficiency is positioned farther from the object, will now be described below with reference to FIG. 2. In FIG. 2, an X-ray tube 11 and a cassette 13 containing stimulable phosphor sheets 12a, 12b, 12c, ..., 12n stacked in such a way that a phosphor sheet exhibiting a higher X-ray use efficiency is positioned farther from an object 14 are positioned on opposite sides of the object 14.

In the recording step, the object 14 is exposed to X-rays emitted from the X-ray tube 11 while the X-ray tube 11 and the cassette 13 are moved in the directions of the arrows 15 and 16, respectively. As a result, tomographic images of tomographic planes 18a, 18b, 18c, ..., 18n of the object 14 are sequentially stored as the X-ray energy in the stimulable phosphor sheets 12a, 12b, 12c, ..., 12n, respectively. At this stage, since the stimulable phosphor sheets 12a, 12b, 12c, ..., 12n are stacked in such a way that a phosphor sheet exhibiting a higher X-ray use efficiency is positioned farther from the object 14, the X-ray energy transmitting through the object 14 is absorbed by the phosphor sheets in an amount approximately uniformly distributed among the phosphor sheets. Accordingly, the stimulable phosphor sheets 12a, 12b, 12c, ..., 12n store tomographic images of the tomographic planes 18a, 18b, 18c, ..., 18n of approximately the same level, and yield visible tomographic images of a uniform quality of the level suitable for viewing and diagnostic purposes. The stimulable phosphor sheets 12a, 12b, 12c, ..., 12n carrying the tomographic images are then sent to a read-out system, and the radiation images are read out from the phosphor sheets and reproduced to visible images in the same way as described above.

Figure 3:
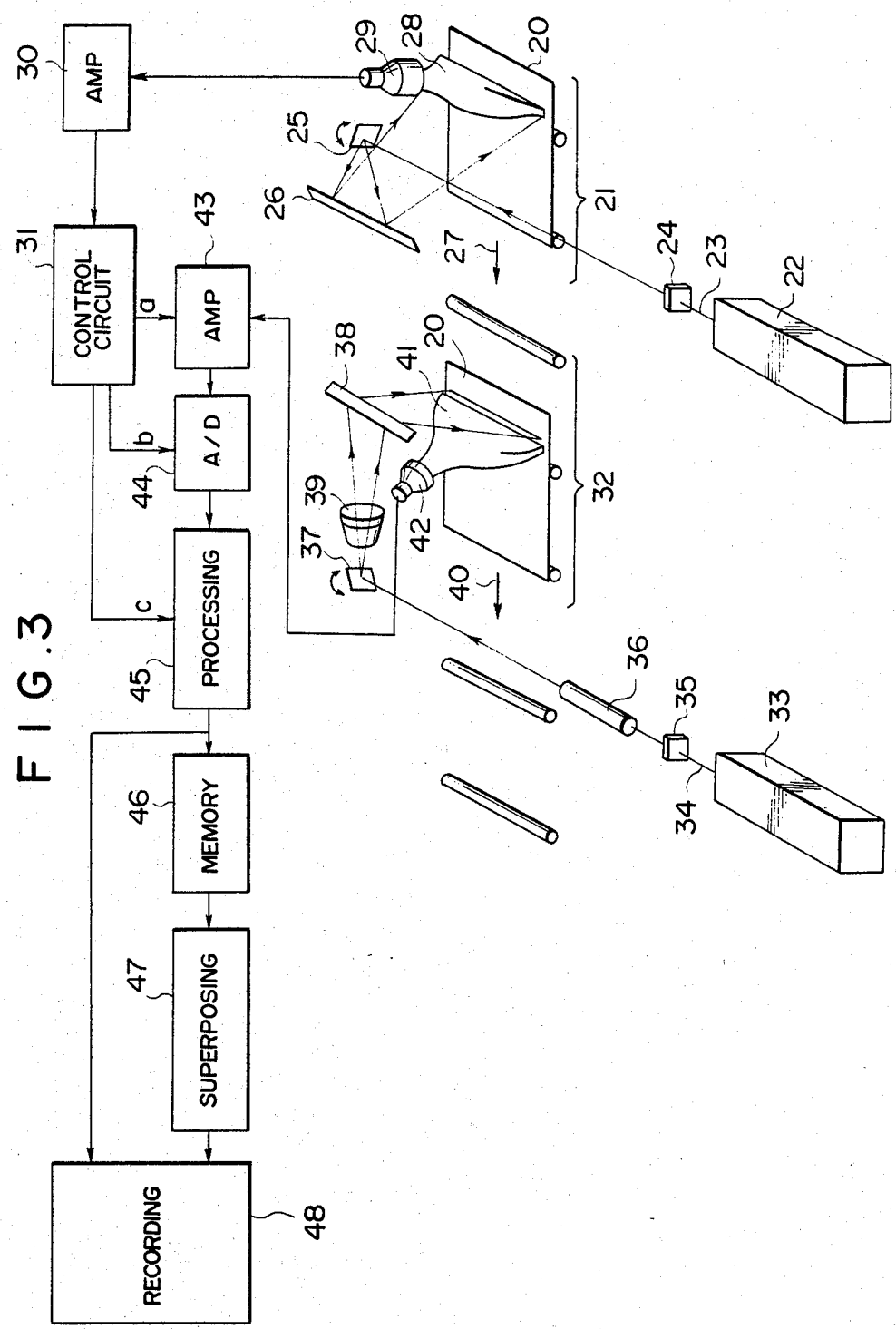
FIG. 3 is a schematic diagram showing a read-out system for carrying out the method in accordance with the present invention.

FIG. 3 shows a read-out system for carrying out the method in accordance with the present invention. The read-out system comprises a preliminary read-out section 21 for reading out information on the X-ray energy stored in the stimulable phosphor sheets 12a, 12b, 12c, ..., 12n which is used to set the read-out gain and the gradation processing conditions, and a final read-out section 32 for reading out the radiation image information stored in the stimulable phosphor sheets 12a, 12b, 12c, ..., 12n to output the radiation image for use in diagnosis.

In the preliminary read-out section 21, a laser beam 23 emitted from a laser source 22 is first passed through a filter 24 for cutting off the light beam having a wavelength within a range identical with the range of the wavelength of the light emitted from a stimulable phosphor sheet 20 upon stimulation by the laser beam 23. Then, the laser beam 23 is one-dimensionally deflected by a light deflector 25 such as galvanometer mirror and directed onto the stimulable phosphor sheet 20 by a plane reflection mirror 26. As the laser source 22 is selected a laser source emitting a laser beam 23 having a wavelength distribution different from and far apart from the wavelength distribution of the light emitted from the stimulable phosphor sheet 20. While the laser beam 23 impinges upon the stimulable phosphor sheet 20, the phosphor sheet 20 is moved in the direction of the arrow 27 and, consequently, the whole area of the phosphor sheet 20 is exposed to and scanned with the laser beam 23. The power of the laser source 22, the beam diameter of the laser beam 23, the scanning speed of the laser beam 23, and the moving speed of the phosphor sheet 20 are selected so that the energy of the laser beam 23 for preliminary read out is smaller than the energy of the laser beam for final read out. When exposed to the laser beam 23, the stimulable phosphor sheet 20 emits light in the pattern of the X-ray energy stored therein, and the emitted light enters a light guiding sheet 28. The light guiding sheet 28 has a linear light input face positioned close to the scanning line on the stimulable phosphor sheet 20, and a ring-shaped light output face in close contact with the light receiving face of a photodetector 29, which may be a photomultiplier. The light guiding sheet 28 is formed of a transparent thermoplastic resin sheet such as an acrylic resin sheet so that the light entering from the light input face can be transmitted to the light output face by total reflection through the interior of the light guiding sheet 28. The light emitted from the stimulable phosphor sheet 20 upon stimulation thereof is guided in the interior of the light guiding sheet 28, emitted from the light output face of the light guiding sheet 28 and received by the photodetector 29. The light guiding sheet 28 may be of a shape and a material as disclosed in U.S. Pat. No. 4,346,295.

The light receiving face of the photodetector 29 is provided with a filter for transmitting only the light having the wavelength distribution of the light emitted from the stimulable phosphor sheet 20 and cutting off the light having the wavelength distribution of the stimulating ray, so that the photodetector 29 can detect only the light emitted from the stimulable phosphor sheet 20 upon stimulation thereof. The light detected by the photodetector 29 is converted to an electric signal and then amplified by an amplifier 30. The X-ray energy information thus read from the stimulable phosphor sheet 20 is then sent from the amplifier 30 to a control circuit 31 of the final read-out section 32.

On the basis of X-ray energy information, the control circuit 31 generates an amplification degree setting value (a), a scale factor setting value (b) and an image processing condition setting value (c) for obtaining a tomographic image having a uniform density and contrast and suitable for viewing and diagnostic purposes. When the preliminary read-out is finished as described above, the stimulable phosphor sheet 20 is sent to the final read-out section 32.

In the final read-out section 32, a laser beam 34 emitted from a laser source 33 is first passed through a filter 35 for cutting off the light beam having a wavelength within the range identical with the range of the wavelength of the light emitted from the stimulable phosphor sheet 20 upon stimulation by the laser beam 34. Then, the beam diameter of the laser beam 34 is strictly adjusted by a beam expander 36. The laser beam 34 is then deflected by a light deflector 37 formed of a galvanometer mirror or the like, and directed onto the stimulable phosphor sheet 20 by a plane reflection mirror 38. Between the light deflector 37 and the plane reflection mirror 38 is positioned an fθ lens 39 for maintaining the beam diameter of the laser beam 34 uniform during the scanning of the laser beam 34 on the stimulable phosphor sheet 20. While the laser beam 34 impinges upon the stimulable phosphor sheet 20, the phosphor sheet 20 is moved in the direction of the arrow 40 and, consequently, the whole area of the phosphor sheet 20 is exposed to and scanned with the laser beam 34. Upon exposure to the laser beam 34, the stimulable phosphor sheet 20 emits light in the pattern of the X-ray energy stored therein, and the light emitted enters a light guiding sheet 41 which is made of the same material and has the same construction as the light guiding sheet 28 used for preliminary read-out. The light emitted from the stimulable phosphor sheet 20 is guided in the interior of the light guiding sheet 41 through total reflection, emitted from the light output face of the light guiding sheet 41 and received by a photodetector 42. The light receiving face of the photodetector 42 is closely contacted with a filter for selectively transmitting only the light having the wavelength distribution of the light emitted from the stimulable phosphor sheet 20, so that the photodetector 42 can detect only the light emitted therefrom. The light detected by the photodetector 42 is converted to an electric signal, amplified to an appropriate level by an amplifier 43 the sensitivity of which has been set by the amplification degree setting value (a), and then inputted into an A/D converter 44. In the A/D converter, the electric signal is converted to a digital signal with a scale factor which has been set by the scale factor setting value (b) to suit the width of signal fluctuation. The digital signal thus obtained is inputted into a signal processing circuit 45, in which it is processed based on the image processing condition setting value (c) so as to obtain a tomographic image having a uniform density and contrast and suitable for viewing and diagnostic purposes. The signal thus processed is sent to a recording section 48.

In another embodiment of the method in accordance with the present invention, the signal obtained from the signal processing circuit 45 in the same way as described above is once stored in a memory 46, instead of being directly sent to the recording section 48. Namely, the stimulable phosphor sheets 12a, 12b, 12c, ..., 12n are sequentially read out as described above, and the obtained tomographic image information of the respective tomographic planes of the object are stored in the memory 46. The pieces of tomographic image information thus stored in the memory 46 are then superposed one upon another in a superposition circuit 47, and sent to the recording section 48 to reproduce the superposed information into a visible image.

Figure 4:
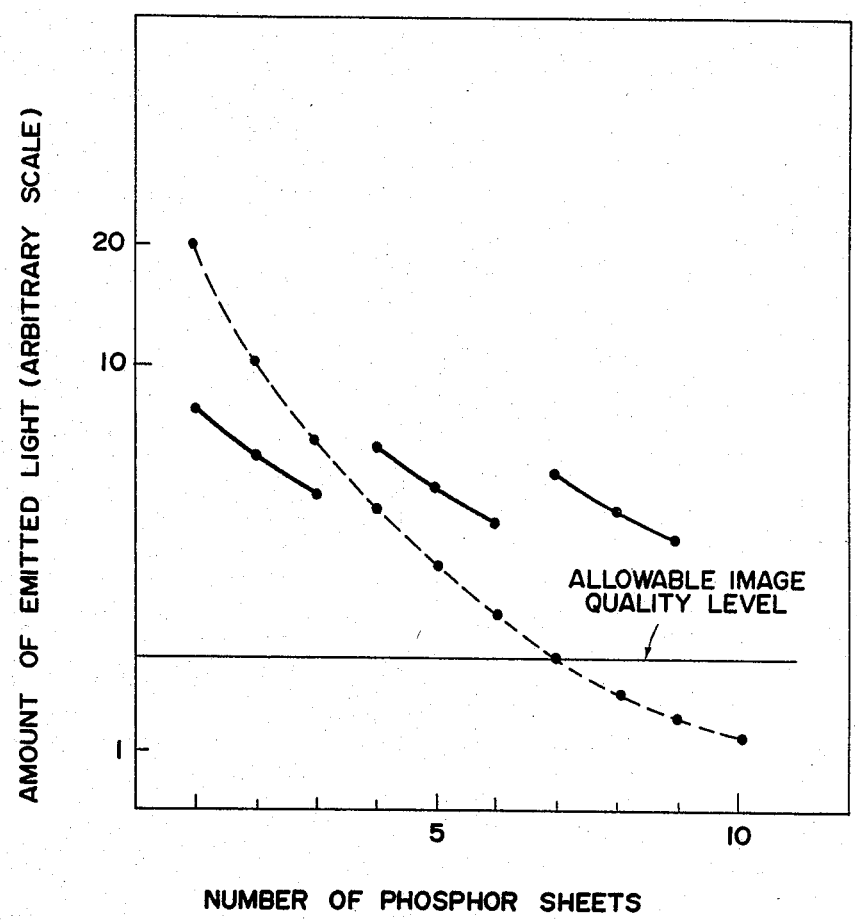
FIG. 4 is a graph showing the relationship between the number of stimulable phosphor sheets stacked to store tomographic images in the method in accordance with the present invention and the amount of light emitted from the phosphor sheets upon stimulation thereof by a stimulating ray.

FIG. 4 shows the relationship between the number of the stimulable phosphor sheets stacked to store tomographic images and the amount of light emitted from the phosphor sheets upon stimulation thereof by a stimulating ray. In FIG. 4, the curve indicated by the broken line was obtained by stacking ten phosphor sheets respectively provided with a phosphor layer formed of the same kind of stimulable phosphor and having the same thickness (i.e. the phosphor sheets having the same specifications), using the stack for tomography, exposing the respective phosphor sheets to a stimulating ray to cause them to emit light, and plotting the amounts of the emitted light with respect to the sheet numbers of the respective phosphor sheets, counted from the top. As shown in FIG. 4, the amount of light emitted from the tenth phosphor sheet is about one-twentieth as large as that of light emitted from the first phosphor sheet. When the phosphor sheets having the same specifications are used, from the first to seventh phosphor sheets can exhibit an image quality sufficient for diagnosis and, thus, it is possible to obtain more tomographic images with one recording step than in the conventional method.

The curves indicated by the solid lines in FIG. 4 were obtained by using three sets of three phosphor sheets respectively provided with a phosphor layer formed of the same kind of stimulable phosphor and having a thickness equal to one another in the same set but different from the thickness in the other sets. These nine phosphor sheets were stacked in such a manner that a set of three phosphor sheets provided with a thinner phosphor layer were positioned above those provided with a thicker phosphor layer, and exposed to X-rays emitted at a tube voltage of 120kVp. Thereafter, the respective phosphor sheets were exposed to a stimulating ray to cause them to emit light, and the amounts of the emitted light were plotted with respect to the sheet numbers of the respective phosphor sheets, counted from the top. The solid-line curves indicate that, although the amount of the emitted light slightly fluctuates among the phosphor sheets provided with a phosphor layer of the same thickness, all of the nine phosphor sheets yield tomographic images having a quality sufficient for viewing and diagnostic purposes. Further, the levels of the radiation images stored on the nine phosphor sheets are approximately equal to one another and, therefore, all the tomographic images reproduced from the phosphor sheets have a high signal-to-noise ratio and a high diagnostic efficiency and accurary.

In the stacking method mentioned above with respect to the solid-line curves shown in FIG. 4, it is also possible to change the thickness of the phosphor layers of all phosphor sheets and stack the phosphor sheets so that the thickness of the phosphor layer sequentially increases towards downwards. In this case, uniformity of the quality of the tomographic images can further be improved. It was also found that approximately the same effect can be obtained when the kind of the stimulable phosphor is changed and the thickness of the phosphor layer is maintained constant, and when both kind of the stimulable phosphor and thickness of the phosphor layer are changed. In the recording section 48, the information may be reproduced in various ways; for example, it may be optically recorded on a light-sensitive material by scanning it with a laser beam or the like, electronically displayed on a CRT or the like, recorded by a video tape recorder or a printer, or recorded on a thermosensitive recording material by using heat wave.

It should be understood that the present invention can be modified in various ways. For example, when a photomultiplier is employed as the photodetector 42, the contrast and the density of the respective tomographic images may be made uniform by changing the applied voltage according to the amplification degree setting value (a), instead of amplifying the output of the photodetector 42 to an appropriate level by the amplifier 43. Further, instead of converting the electric signal to a digital signal with a scale factor suitable for the signal fluctuation width in the A/D converter 44, the signal fluctuation width may be optimized according to the scale factor setting value (b) in an analog amplifier, followed by conversion to a digital signal in the A/D converter 44. Furthermore, the X-ray tube and the stimulable phosphor sheets may be moved with respect to each other along a circular, elliptical or spiral path, instead of the linear path, insofar as the linear rule and the geometric rule described above are satisfied.

We claim:

1. A method of recording an X-ray image comprising the steps of: positioning a stack of a plurality of stimulable phosphor sheets and an X-ray tube with an object intervening therebetween, and moving said stack and said X-ray tube with respect to each other in relation to a tomographic plane in said object so as to satisfy the linear rule and the geometric rule in the course of exposure of said object to X-rays, exposing the respective stimulable phosphor sheets to a stimulating ray to cause them to emit light, photoelectrically reading out the light emitted from said stimulable phosphor sheets upon stimulation thereof, and recording an X-ray image using the obtained electric signal or signals.

2. A method as defined in claim 1 wherein said stack comprises a plurality of stimulable phosphor sheets stacked in such a way that a stimulable phosphor sheet exhibiting a higher X-ray use efficiency is positioned farther from the object.

3. A method as defined in claim 2 wherein said stack comprises a plurality of stimulable phosphor sheets stacked in such a way that a stimulable phosphor sheet provided with a thicker phosphor layer is positioned farther from the object.

4. A method as defined in claim 2 wherein said stack comprises a plurality of stimulable phosphor sheets stacked in such a way that a stimulable phosphor sheet provided with a phosphor layer formed of a stimulable phosphor exhibiting a higher X-ray use efficiency is positioned farther from the object.

5. A method as defined in claim 1 wherein each stimulable phosphor sheet is provided with a layer of stimulable phosphor for emitting light having a wavelength within the range between 300 nm and 500 nm upon stimulation thereof.

6. A method as defined in claim 5 wherein said stimulable phosphor is a rare earth activated alkaline earth metal fluorohalide phosphor.

7. A method as defined in claim 6 wherein said stimulable phosphor is a barium fluorohalide phosphor.

8. A method as defined in claim 1 further comprising the step of exposing the respective stimulable phosphor sheets image-wise radiation exposure to produce tomographic images stored therein.

9. A method as defined in claim 8 wherein said stimulating ray has a wavelength within the range between 450 nm and 700 nm.

10. A method as defined in claim 8 wherein the respective stimulable phosphor sheets are first exposed to a stimulating ray for preliminary read-out to photoelectrically read out the radiation energy information necessary for setting image reproducing conditions, and then exposed to a stimulating ray for final read-out to reproduce a visible radiation image under said image reproducing conditions, said preliminary read-out exposure being conducted subsequent to said image-wise radiation exposure.

11. A method as defined in claim 10 wherein said stimulating ray for preliminary read-out has energy lower than the energy of said stimulating ray for final read-out.

12. A method as defined in claim 10 wherein said image reproducing conditions are the read-out gain and/or gradation processing conditions.

13. A method as defined in claim 8 wherein the electric signals obtained by photoelectrically reading out the light emitted from said stimulable phosphor sheets are then sent to a recording apparatus.

14. A method as defined in claim 13 wherein said electric signals are amplified, A/D converted, electrically processed, and then sent to said recording apparatus.

15. A method as defined in claim 8 wherein the electric signals obtained by photoelectrically reading out the light emitted from said stimulable phosphor sheets are then superposed one upon another.

16. A method as defined in claim 15 wherein said electric signals are amplified, A/D converted, electrically processed, stored in a memory, and then superposed one upon another.

17. A method as defined in claim 15 wherein the superposed electric signals are sent to a recording apparatus.

18. A method as defined in claim 8 wherein said step of exposing the respective stimulable phosphor sheets to a stimulating ray comprises two-dimensionally scanning said stimulable phosphor sheets with a stimulating ray.

19. A method as defined in claim 8 wherein said stimulating ray is a laser beam.

20. A method as defined in claim 1 wherein said stack comprises a plurality of stimulable phosphor sheets having the same X-ray use efficiency.

21. A method of recording an X-ray image, said method comprising the steps of:

positioning a stack of a plurality of stimulable phosphor sheets and an X-ray tube with an object intervening therebetween;

moving said stack and said X-ray tube with respect to each other in relation to a tomographic plane in said object so as to satisfy the linear rule and the geometric rule in the course of exposure of said object to X-rays;

exposing the respective stimulable phosphor sheets which have been subjected to image-wise radiation exposure to produce tomographic images stored therein to a stimulating ray to cause them to emit light, said respective stimulable phosphor sheets being first exposed to a stimulating ray for preliminary read-out to photoelectrically read out radiation energy information necessary for setting image reproducing conditions, followed by exposure to a stimulating ray for final read-out to reproduce a visible radiation image under said image reproducing conditions, said preliminary read-out exposure being conducted subsequent to said image-wise radiation exposure;

photoelectrically reading out the light emitted from said stimulable phosphor sheets upon stimulation thereof to produce an electric signal; and recording an X-ray image using the obtained electric signal.

22. A method of recording an X-ray image, said method comprising the steps:

positioning a stack of a plurality of stimulable phosphor sheets and an X-ray tube with an object intervening therebetween;

moving said stack and said X-ray tube with respect to each other in relation to a tomographic plane in said object so as to satisfy the linear rule and the geometric rule in the course of exposure of said object to X-rays;

exposing the respective stimulable phosphor sheets which have been subjected to imagewise radiation exposure to produce tomographic images stored therein to a stimulating ray to cause them to emit light;

photoelectrically reading out the light emitted from said stimulable phosphor sheets upon stimulation thereof to produce electric signals;

recording an X-ray image using the obtained electric signals; and superimposing said electric signals one upon another.

* * * * *